United States Patent [19]

Bokros

[11] Patent Number: 4,639,247
[45] Date of Patent: Jan. 27, 1987

[54] PERCUTANEOUS ACCESS DEVICE
[75] Inventor: Jack C. Bokros, Austin, Tex.
[73] Assignee: Carbomedics, Inc., Austin, Tex.
[21] Appl. No.: 667,581
[22] Filed: Nov. 2, 1984
[51] Int. Cl.$^4$ .............................................. A61M 5/32
[52] U.S. Cl. ..................................... 604/175; 604/33; 604/256
[58] Field of Search .................. 604/175, 29, 33, 52, 604/4–10, 93, 248, 249, 169, 256; 27/24 A

[56] References Cited

U.S. PATENT DOCUMENTS

| | | | |
|---|---|---|---|
| 1,391,464 | 9/1921 | Degenhart | 27/24 A |
| 3,765,032 | 10/1973 | Palma | 604/175 |
| 3,783,868 | 1/1974 | Bokros . | |
| 3,826,257 | 7/1974 | Buselmeier | 604/8 |
| 3,998,222 | 12/1976 | Shibata | 604/9 |
| 4,015,601 | 4/1977 | Bokros et al. . | |
| 4,108,173 | 8/1978 | Slivenko et al. . | |
| 4,108,174 | 8/1978 | Slivenko | 604/175 |
| 4,164,221 | 8/1979 | Bentley et al. | 604/175 |
| 4,180,068 | 12/1979 | Jacobsen et al. | 604/33 |
| 4,181,132 | 1/1980 | Parks | 604/175 |
| 4,349,021 | 9/1982 | Raible . | |
| 4,405,319 | 9/1983 | Cosentino . | |
| 4,405,320 | 9/1983 | Cracauer et al. . | |
| 4,417,888 | 11/1983 | Cosentino et al. . | |
| 4,421,507 | 12/1983 | Bokros . | |

Primary Examiner—Dalton L. Truluck
Assistant Examiner—Mario Costantino
Attorney, Agent, or Firm—Fitch, Even, Tabin & Flannery

[57] ABSTRACT

A percutaneous access device having at least one substantially rectilinear passageway that extends between the internal region of a living body and the region exterior of the body when the device is anchored therein. A second passageway intersects with the first so as to provide communication between the internal region and the exterior region through the lower portion of the first rectilinear passageway and the second passageway. Disposed within the rectilinear passageway is a plunger having a sealing tip on the distal end thereof and access to the internal region of the body is achieved by withdrawing the sealing tip of the plunger past the point where the second passageway intersects the rectilinear passageway. The plunger shaft has a non-uniform cross section along its length and the exterior opening of the rectilinear passageway is in the form of a keyway so that the plunger is movable within the rectilinear passageway only upon selective rotation of the plunger.

13 Claims, 12 Drawing Figures

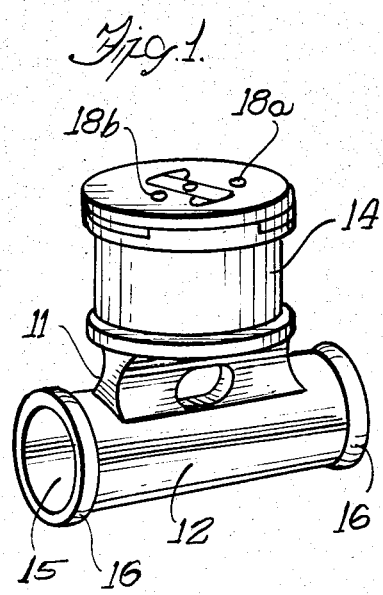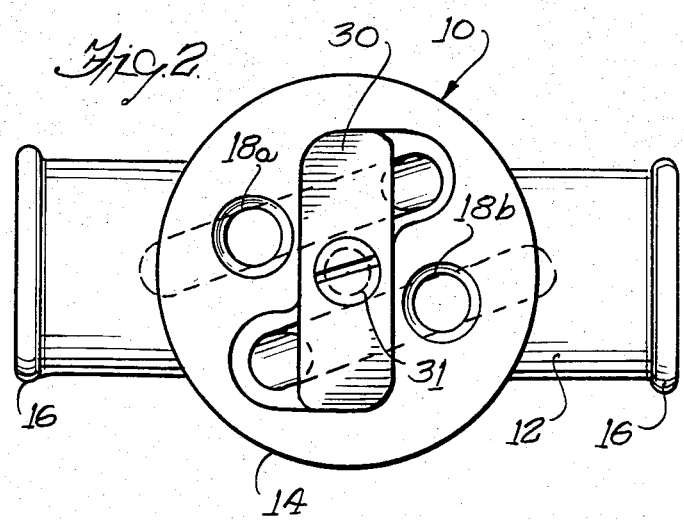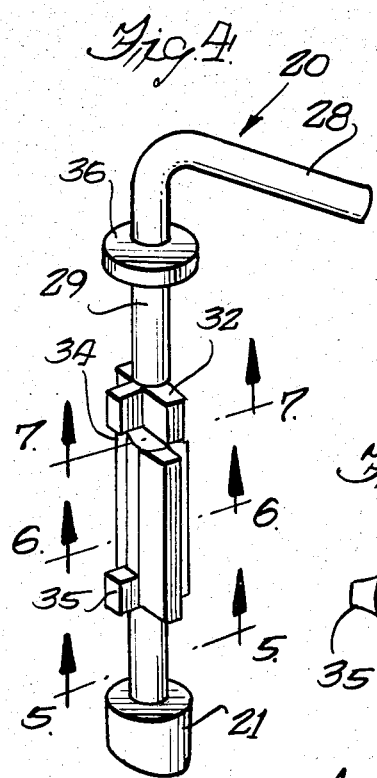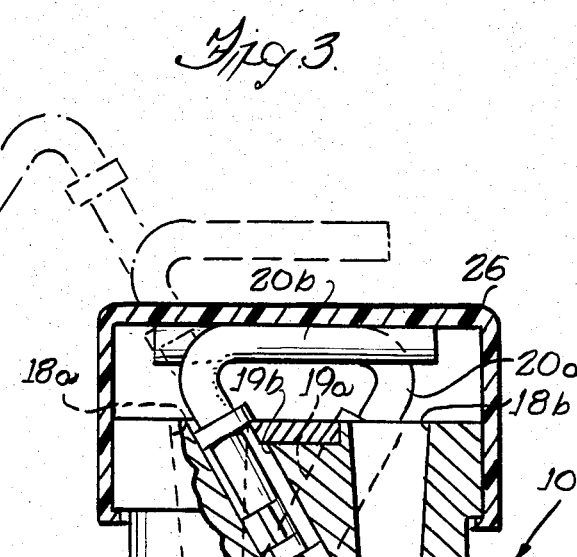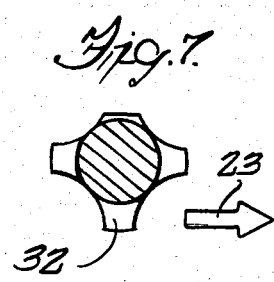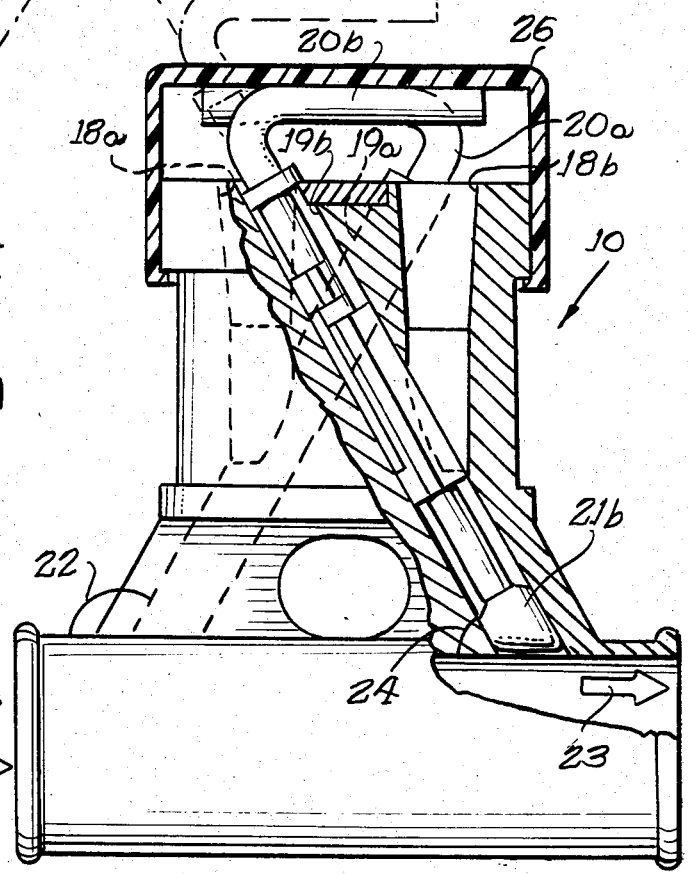

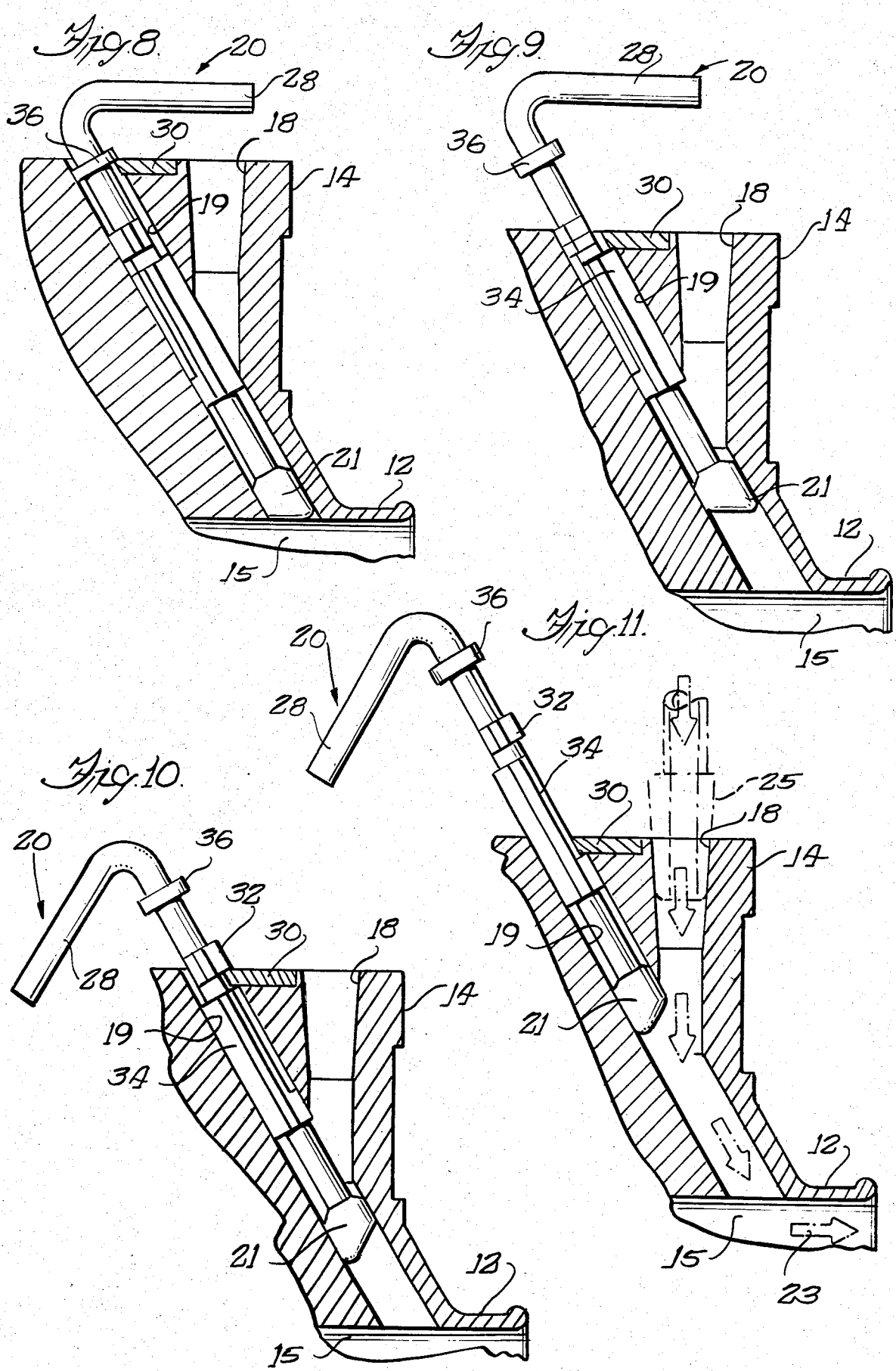

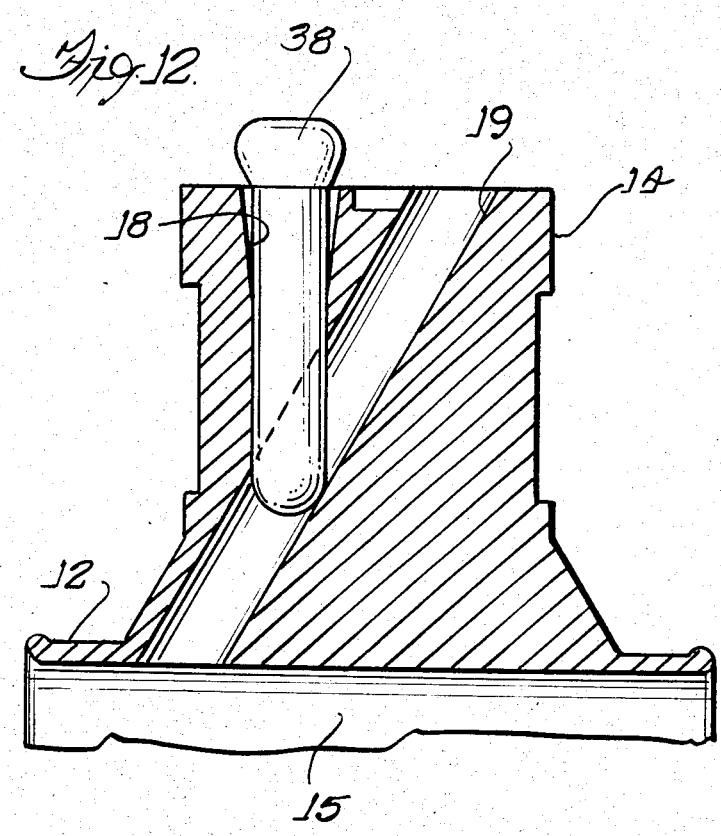

PERCUTANEOUS ACCESS DEVICE

This invention relates to medical devices and more particularly to improvements in such devices that provide access to internal regions of the living body.

BACKGROUND OF THE INVENTION

There is a need for devices to provide access to internal regions of a living body, such as the circulatory system or body cavities, in circumstances requiring, for example, repeated withdrawal of blood, peritoneal dialysis, or injections of drugs, which may be continuous or repeated. While access to the circulatory system is ordinarily gained by use of a needle and syringe, repeated injections may cause scarring and eventual collapse of the vein or infection. Therefore, when repeated injections or blood withdrawals are required, a percutaneous access device is implanted, through which access may be gained to the circulatory system and thereafter closed off.

A number of designs for blood access devices have been developed. Devices utilizing rubber septums have, in particular, been associated with numerous problems. The amount of pressure exerted upon the septum by the blood access device itself is critical for insuring that the device remains sealed. This requires precise machining of such devices, with exacting tolerances and the accompanying high cost. Further, the septums have been susceptible to tearing by the needles utilized to either inject or withdraw liquids through the device, necessitating the difficult operation of replacing the damaged septum. Problems have also developed with devices that use sliding or rotating valves to control access to the circulatory system because blood may seep into the valve mechanism, causing the valve to stick. Such sticking is especially troublesome because a surgically implanted device is not easily accessible for repairs. Furthermore, blood which has seeped into the valve mechanism is a breeding ground for bacteria which may cause infection in the patient, and stagnant blood or denatured protein in the valve mechanism can cause clotting.

All blood access devices are inconvenient and unsightly, and for cosmetic reasons, a blood access device should be as small as possible. However, it is desirable to obtain a fluid flow rate through the device sufficient to perform the required injection or withdrawal in the shortest possible time. Accordingly, the passageway communicating with the region exterior of the body should be designed to minimize the resistance to flow therethrough.

Additionally, a blood access device for permanent implantation in the human body must be biocompatible with body tissue to prevent rejection reactions and associated infection. Surfaces which interface with blood should be thromboresistant to prevent blood clotting.

SUMMARY OF THE INVENTION

A percutaneous access device includes at least one substantially rectilinear passageway that extends between the internal region of a living body and the region exterior of the body when the device is anchored therein. A second passageway intersects with the first so as to provide communication between the internal region and the exterior region through the lower portion of the first rectilinear passageway and the second passageway. Disposed within the rectilinear passageway is a plunger having a sealing tip on the distal end thereof, and access to the internal region of the body is achieved by withdrawing the sealing tip of the plunger past the point where the second passageway intersects the rectilinear passageway. The plunger shaft has a non-uniform cross section along its length, and the exterior opening of the rectilinear passageway is in the form of a keyway so that the plunger is movable within the rectilinear passageway only upon selective rotation of the plunger.

BRIEF DESCRIPTION OF THE DRAWINGS

FIG. 1 is a perspective view of the valve body of a percutaneous access device in accordance with the present invention.

FIG. 2 is an enlarged top plan view of the percutaneous access device of FIG. 1;

FIG. 3 is a front elevation view in partial cross-section of the percutaneous access device of FIG. 2;

FIG. 4 is a perspective view of the plunger and sealing plug that forms a part of the invention;

FIG. 5 is a cross-sectional view of the plunger taken substantially along line 5—5 of FIG. 4;

FIG. 6 is a cross-sectional view of the plunger taken along line 6—6 of FIG. 4;

FIG. 7 is a cross-sectional view of the plunger taken along line 7—7 of FIG. 4;

FIGS. 8-11 are partial cross-sectional views of a plunger and its associated passageways illustrating the sequence of withdrawal of the plunger to provide access between the interior and exterior regions of a body; and FIG. 12 is a partial cross-sectional view of the percutaneous access device with the plunger completely withdrawn and the passageways sealed by an auxiliary plug.

DETAILED DESCRIPTION OF THE PREFERRED EMBODIMENT

Turning now particularly to FIGS. 1-3, there is seen a percutaneous access device, generally indicated by 10, according to the present invention. The device 10 includes a T-shaped valve body or housing 11, shown in perspective in FIG. 1. The valve body 11 includes an integral flow tube or conduit 12 for insertion into the circulatory system of a living body. Extending upward from the conduit 12 is an upright structure 14 that will extend through the skin when the device is implanted in a living body and through which access to the conduit 12 is gained. (To aid description, "lower" or "downward" are used herein to denote the direction toward the interior of the body, while "upper" or "upward" are used to describe the direction toward the exterior of the body.)

The conduit 12 of the percutaneous access device 10 is generally cylindrical in shape and has a smooth cylindrical central passageway 15 for unhindered flow therethrough. The conduit 12 can be inserted in line with a blood vessel by means of any of the well-known techniques, with ridges 16 on the exterior of the conduit 12 providing for a more-secure attachment between the blood vessel and the conduit. The valve body 10 should be strong and durable and its surfaces should be biocompatible and thromboresistant. Accordingly, the valve body 11 may be made of metals such as titanium, stainless steel or chromium-cobalt alloys, or the surfaces of the valve body 11 may be made biocompatible and thromboresistant by coating them with carbon by vapor deposition as described in U.S. Pat. No. 3,952,336, issued Apr. 27, 1976 to Bokros, et al.

In accordance with the invention, the valve housing 11 is provided with at least one pair of intersecting passages and a cooperating plunger to provide access to the central passageway 15 of the conduit 12 from the region exterior of the body upon selective withdrawal of the plunger. With reference to the illustrated embodiment, which is particularly suited for use in conjunction with procedures requiring the simultaneous withdrawal from and injection into the bloodstream of a human body, the upright structure 14 includes a pair of access ports 18 each intersecting a substantially rectilinear passageway 19 that extends between the top of the upright structure 14 exterior of the body and the conduit 12. Disposed within each passageway 19 is a plunger 20, preferably made of titanium, having a sealing tip 21 disposed on the distal end thereof. The plunger 20, as best seen in FIG. 4, has a complex shape and is preferably injection-molded from a suitable thermoplastic resin, or the like, such as a polysulfone. The sealing tip 21 is preferably made of a resilient material, such as silicone rubber, and is sized in diameter to rub against the inner surface of the rectilinear passageway 19 as the plunger 20 is being inserted or withdrawn. Thus, flow past the sealing tip is prevented and the sealing tip wipes the inner surface of the passageway 19 to help keep it clean. In order to establish a flow pattern between the conduit 12 and the region exterior of the body, the plunger 20 and its associated sealing tip 21 are withdrawn past the intersection of the rectilinear passageway 19 with the access port 18 while a cannula 25 is inserted into the exterior opening of the access port 18, as illustrated in FIG. 11.

In order to minimize the resistance to flow through the device 10 when the device is implanted in an environment in which there is a constant flow in a single direction through the device (such as a bloodstream), the rectilinear passageways 19a, 19b are disposed in oblique relationship with respect to each other and to the conduit 12. Thus, the lower portion of each passageway 19 will be at an angle with respect to both its associated access port 18 and the central passageway 15 of the conduit 12. More particularly, the rectilinear passageway 19a forms an obtuse angle 22 (as measured with respect to the flow direction through the conduit 12 as indicated by arrows 23) while the rectilinear passageway 19b forms an acute angle 24 with respect to the conduit. Preferably angle 22 measures approximately 120°, while angle 24 measures approximately 60°. The angled portion of the flow path provides for a more gradual change of direction of the fluid flowing between the access port and the conduit, and thus less turbulence will be generated when fluid is either withdrawn from or injected into the bloodstream. In practice, assuming a flow through the conduit from left to right as indicated by the arrows 23, fluid will be withdrawn through access port 18a and the lower portion of passageway 19a, while fluid will be injected into the bloodstream through access port 18b and the lower portion of passageway 19b.

To reduce the resistance of flow through the central passageway 15 of the conduit 12 when the plungers 20 are fully inserted into their respective passageways 19, the sealing tips 21 are beveled at an angle substantially equal to the angle that each plunger's respective passageway makes with respect to the conduit 12. Thus, the sealing tips will be flush with the intersection of the passageways with the conduit and the flow through the conduit will remain substantially linear, rather than having eddies being formed by a discontinuity at the conjunction of the internal opening of the passageway 19, the sealing tip 21 and the sealed passageway 15.

When the device 10 is not in use and the plungers 20 are fully inserted into the device, accidental manipulation of the plungers 20 to open the flow passages can be prevented by means of a cap 26 that fits over the top of the upright structure 14 of the valve body 11 to cover the plungers and the access ports. Such a cap 26 may be selectively secured to the valve body by a bayonet-type locking means, as illustrated, or the cap and valve body may be threaded, or snapped together, etc.

In accordance with the invention, the plungers 20 and their associated sealing tips 21 can be selectively positioned along the length of the passageway to permit either access to the flow path or to simultaneously seal the flow tube 12 and permit the cleaning of the passageway and access port. Further, each plunger 20 is configured so that in order to withdraw or insert its sealing tip 21 to its selective locations along the length of the passageway, the plunger 20 must be rotated to a specific position before it can be further inserted or withdrawn.

Referring to FIG. 4, a plunger 20 is shown in perspective. The plunger 20 includes a handle or grip portion 28 disposed from the shaft 29 of the plunger at an angle equal to the angle that its passageway 19 makes with respect to conduit 12. Thus, when the plunger 20 is fully inserted into its passageway 19, the plunger can be rotated so that the handle portion 28 lies along the upper surface of the upright structure 14 and within the outside diameter of the same so that the handles 28 have a low profile, making the device less conspicuous, and permitting the handles 28 to fit underneath the cap 26.

Referring to FIG. 2, a substantially rectangular access plate 30 is removably secured in a recess in the upper surface of the upright structure 14 by means of a screw 31 so that the edges of the access plate 30 partially block and truncate the elliptical-shaped exterior openings of the passageways 19a, 19b. As seen in FIG. 3, the edge of the access plate 30 that blocks the openings of the passageways 19 may be beveled so as to be parallel with the axes of the passageways. In order to restrict the travel of the plunger 20 into or out of its associated passageway 19, the cross section of the shaft is non-uniformly configured so that at selected locations along its length, so that, absent rotation of the shaft, the shaft will abut the access plate, thereby preventing further linear movement of the plunger.

As illustrated, the plunger shaft includes T-shaped cross-sections 32, 34 near the upper end of plunger 20, shown in FIGS. 7 and 6, respectively, and, adjacent the sealing tip 21, an X-shaped cross section 35, shown in FIG. 5. The crossbars of the X- and T-shaped sections are substantially equal in length to the diameter of the passageways 19. The T-shaped cross-sections 32, 34 may be rotated so that the crossbar of the T is parallel to and spaced from the lateral edge of the access plate 30, with the other bar of the T pointing away from the access plate 30, to permit insertion or withdrawal of the plunger 20. Accordingly, when properly oriented with respect to the access plate, the plunger may be withdrawn or inserted. However, the X-shaped cross-section 35 cannot be withdrawn past the access plate 30 regardless of its orientation with respect thereto. The plunger shaft also includes a circular collar 36 at its upper end which acts as a stop that will abut the access plate 30 to limit the insertion of the plunger 20 into its passageway 19.

In order to better explain the cooperating nature of the plunger shaft with the access plate, the operation of the device so as to provide access to the bloodstream through one of the ports will be described. Referring to FIG. 8, the plunger 20 is in its closed position with the sealing tip 21 flush with the central passageway 15 of the conduit 12. In this position, the collar 36 abuts the upper edge of the access plate 30 to prevent further insertion of the plunger 20 into the device. Without rotating the plunger, it may be partially withdrawn to the position shown in FIG. 9, where the T-shaped cross-section 32 has cleared the access plate 30, while the T-shaped cross-section 34 abuts the cross section to prevent further withdrawal of the plunger. In this position, the sealing tip 21 is disposed below the intersection of the rectilinear passageway 19 with the access port 18, thus preventing any flow between the central passageway 15 and the exterior of the device. At this time, a cannula 25, such as that shown in FIG. 11, may be inserted into the access port 18. Before the plunger can be further withdrawn, it must be rotated 180° to the position shown in FIG. 10 so that the T-shaped cross section 34 will clear the access plate 30. In this position, the handle 28 of the plunger will be pointing downward and outward from the upright structure 14, thus providing an approximate indication of the proper orientation of the plunger 20 with respect to the access plate that will permit further withdrawal. Upon proper orientation, the plunger 20 may be withdrawn to the position shown in FIG. 11, with sealing tip 21 being located in the passageway 19 upward from the intersection of the passageway 19 with the access port 18, thus allowing flow between the exterior of the device and the central passageway 15. In this position, the X-shaped cross-section 35 of the plunger shaft abuts the access plate 30 to prevent further withdrawal of the plunger 20 from the device. In the illustrated embodiment, the two plungers 20a, 20b may be simultaneously withdrawn to permit concurrent withdrawal from and injection into the body.

In order to insert the plunger 20 after access has been provided, the procedure is reversed. When the plunger 20 has been returned to its position as shown in FIG. 9, it may be desired to flush the access port 18 and passageway 19 by injecting a disinfectant solution into the access port 18 by means of a cannula, such as that illustrated at 25, the disinfectant solution exiting the device through the upper opening in the passageway 15. Consequently, bacterial growth and the possibility of infection are minimized. After the plunger is returned to the position shown in FIG. 8, the cap 26 may be secured to the device to prevent accidental or unintentional manipulation and withdrawal of the plungers 20.

On occasion, it may be desired to completely remove the plungers 20 from the device in order to replace or repair the same. In such circumstances, the screw 31 will be removed and the access plate 30 withdrawn from its recess simultaneously with the withdrawal of the plungers 20. Concurrently, an auxiliary plug 38, shown in FIG. 12, will be inserted into the access port 18 to seal the passageway. Thus, servicing of all the movable parts of the device is easily accomplished.

Although the invention has been described with regard to a certain preferred embodiment, it should be understood that various changes and modifications as would be obvious to one having ordinary skill in the art may be made without departing from the scope of the invention which is defined solely by the appended claims.

What is claimed is:

1. An implantable device comprising
   a housing having one end which is implantable in a patient and a second end which extends external of the patient when implanted,
   said housing having a substantially rectilinear first passageway of substantially constant cross-section extending between an opening in the first end of said housing and a first opening in the second end of said housing,
   said housing also having a second passageway extending through the housing from a second opening in the second end to a junction iwth said first passageway located between said openings in said first and second ends so as to provide communication between said first passageway and a region exterior of the body through said second passageway,
   a plunger desposed within said first passageway through said first opening comprising a shaft having a cross-section that is smaller than the cross-section of said first passageway and also having sealing means on the distal end thereof which seals with the interior wall of said first passageway throughout substantially the entire length thereof, access to said opening in said one end through said second passageway being achieved only upon withdrawal of said plunger and its associated sealing means past the junction between said second passageway and said first passageway, said shaft of said plunger being of such length that, when said plunger is fully inserted into said first passageway, said sealing means extends substantially to said opening in the said first end and not therebeyond.

2. The device of claim 1 further comprising means associated with said plunger and housing to permit withdrawal of said plunger past said junction only upon selective rotation of said plunger.

3. The device of claim 2 wherein the selective withdrawal means associated with said plunger comprises a non-uniform cross-section shape of said plunger shaft along the length thereof, and removable access plate means partially blocking said first opening of said first passageway so as to form a keyway for said plunger shaft.

4. The device of claim 1 further comprising cap means overlying a handle portion of said plunger, which is disposed at an acute angle to said shaft portion, and being selectively removable from said second end of the housing, which cap means prevents access to said plunger when said plunger is fully inserted into said rectilinear first passageway and said cap means is in place on said housing.

5. The device of claim 1 further comprising auxiliary removable plug means disposed within said second passageway with said plunger withdrawn past said junction, said plug means being proportioned to seal communication to said opening in said first end through both said first and second passageways.

6. The device of claim 1 further comprising a substantially rectilinear third passageway in said housing extending between another opening in said first end and a third opening in said first end and a third opening in said second end, a fourth passageway in said housing extending through said housing from a fourth opening in said second end to a junction with said third passageway located between said openings in said first and second ends so as to provide communication between said third passageway and a region exterior of the body through said fourth passageway, a second plunger disposed within said third passageway through said third opening comprising a shaft that is smaller in cross-section than the cross-section of said third passageway and that has sealing means on the distal end thereof which seals with the interior wall of said third passageway throughout substantially the entire length thereof, access of said another opening in said one end through said fourth passageway being achieved only upon withdrawal of said second plunger and its associated sealing means past the junction between said fourth passageway and said third passageway, said shaft of said second plunger being of such length that, when said second plunger is fully inserted into said third passageway, said sealing means thereon extends substantially to said another opening in the first end.

7. The device of claim 6 wherein said shaft portion of said second plunger has a non-uniform cross-section shape, and wherein removable access plate means partially blocks said third opening of said third passageway so as to form a keyway for said second plunger shaft which permits withdrawal past the junction between said third and fourth passageways only following selection rotation of said second plunger.

8. The device of claim 7 wherein said housing includes a conduit portion a straight passage therethrough as a part of said one end, with said openings in said one end being located in the interior wall of said conduit portion, said substantially rectilinear first and third passageways being in oblique relationship with the straight passage through said conduit portion, said first passageway forming an obtuse angle with respect to the conduit passage in one direction and said third passageway forming an acute angle with respect to the conduit passage in said same one direction 9. The device of claim 8 wherein said first passageway forms an angle of approximately 120° with respect to the conduit passage and said third passageway forms an angle of approximately 60° with respect to the conduit passage.

10. The device of claim 9 wherein said sealing means on the distal ends of said respective plungers are beveled at an angle substantially equal to the angle that each said plunger's respective passageway makes with respect to the conduit passage so that, when said plungers are fully inserted into their respective passageways, said respective sealing means are substantially flush with the interior wall of the conduit passage.

11. An implantable device comprising
a housing having one end which is implantable in a patient and a second end which extends external of the patient when implanted,
said housing having a substantially rectilinear first passageway of substantially constant cross-section extending between an opening in said first end of said housing and a first opening in said second end of said housing,
said housing also having a second passageway extending through the housing from a second opening in said second end to a junction with said first passageway located between said openings in said first and second ends so as to provide communication between said first passageway and a region exterior of the body through said second passageway,
a plunger disposed within said first passageway through said first opening comprising a shaft having an irregular cross-section that is smaller then the cross-section of said first passageway and that varies along the length of the plunger and also having sealing means on the distal end thereof which seals with the interior wall of said first passageway throughout substantially the entire length thereof, said housing having means permitting partial axial withdrawal of said plunger so said sealing means is located adjacent the junction of said passageways where there is communication between said first and second openings of said passageways through the junction and past said irregular cross-section shaft, access to said opening in said one end through said second passageway being achieved only upon selective rotation of said plunger in the partially axially withdrawn location and then withdrawal of said plunger and its associated sealing means past the junction between said second passageway and said first passageway, said shaft of said plunger being of such length that, when said plunger is fully inserted into said first passageway, said sealing means extends past said junction but not substantially beyond said opening in the first end.

12. The device of claim 11 further comprising a handle portion associated with said plunger which is oriented at an acute angle to said shaft of said plunger and which allows selective rotation of said plunger only following partial withdrawal.

13. The device of claim 12 wherein removable access plate means attached to said first end of said housing partially blocks said first opening of said first passageway so as to form a keyway for said irregular cross-section shape of said plunger shaft.

* * * * *